US005720980A

United States Patent [19]

Cohen

[11] Patent Number: 5,720,980

[45] Date of Patent: Feb. 24, 1998

[54] PLANT PROTECTION USING FISH OIL

[75] Inventor: Yigal Cohen, Kiryat Ono, Israel

[73] Assignee: Bar-Kan University, Ramat gan, Israel

[21] Appl. No.: 585,126

[22] Filed: Jan. 11, 1996

Related U.S. Application Data

[63] Continuation-in-part of Ser. No. 200,332, Feb. 23, 1994, Pat. No. 5,494,684.

[51] Int. Cl.$^6$ .............................. A61K 35/60; C05F 1/00; C05F 31/59

[52] U.S. Cl. .......................... 424/523; 424/554; 424/555; 71/16; 504/320; 504/357

[58] Field of Search ..................................... 424/523, 554, 424/555; 71/16; 504/320, 357

[56] References Cited

U.S. PATENT DOCUMENTS

| | | | |
|---|---|---|---|
| 108,030 | 10/1870 | Kepner | 424/523 |
| 111,185 | 1/1871 | Everett | 424/523 |
| 2,013,063 | 9/1935 | Miller . | |
| 2,128,973 | 9/1938 | Tisdale et al. . | |
| 2,198,991 | 4/1940 | Dutton . | |
| 3,712,803 | 1/1973 | Grybek et al. . | |
| 3,725,557 | 4/1973 | Douros, Jr. et al. . | |
| 3,728,454 | 4/1973 | Douros, Jr. et al. . | |
| 3,896,230 | 7/1975 | Klopping | 424/523 |
| 4,043,788 | 8/1977 | Fryer . | |
| 4,254,112 | 3/1981 | Debat et al. . | |
| 4,599,233 | 7/1986 | Misato et al. . | |
| 4,681,617 | 7/1987 | Ghyczy et al. . | |
| 4,761,423 | 8/1988 | Szego et al. | 514/395 |
| 4,826,863 | 5/1989 | Szego et al. | 514/395 |
| 4,885,177 | 12/1989 | Wegmann | 424/523 |
| 4,888,325 | 12/1989 | Schroeder et al. . | |
| 5,176,913 | 1/1993 | Honerlagen et al. . | |

OTHER PUBLICATIONS

Cohen, Y. et al, "Systemic Resistance of Potato Plants Against *Phtophthora Infestans* Induced by Unsaturated Fatty Acids", Physiological and Molecular Plant Pathology 38: 255–263 (1991).

Banhamou, N. et al, "Immunogold Localization of Pathenogenesis–related protein P14 in Tomato Root Cells infected by *Fusarium Oxysporum* f. sp. *Radicis–Lycopersici*" Physiological and Molecular Plant Pathology 38: 237–253 (1991).

Kirk–Othmer, "Encyclopedia of Chemical Technology" 3rd Ed vol. 9 pp 798–799, 804–805.

*Primary Examiner*—Leon B. Lankford, Jr.
*Assistant Examiner*—Francisco C. Prats
*Attorney, Agent, or Firm*—Mark M. Friedman

[57] ABSTRACT

A composition for protecting a crop against fungal diseases which includes one or more fish oils used in association with an agriculturally acceptable diluent and, preferably, with a metal salt. Also provided is a method for protecting a crop against fungal diseases which includes applying to the seed or foliage of a crop or its locus, a fish oil in an amount sufficient to induce the local and/or systemic resistance of the crop to control the fungal disease.

21 Claims, 6 Drawing Sheets

PLANT PROTECTION USING FISH OIL

This is a Continuation-in-Part of U.S. patent application Ser. No. 08/200,332, filed Feb. 23, 1994, now U.S. Pat. No. 5,494,684.

FIELD AND BACKGROUND OF THE INVENTION

The present invention relates to the use of materials for protecting crops from pathogenic attack.

In particular, the present invention relates to the use of fish oils and novel compositions containing the fish oils, which upon application to a crop, protect the crop against fungal infections. The prior art teaches a wide variety of materials which protect plants and enhance their growth. For example, U.S. Pat. No. 3,712,803 discloses the use of an aqueous mixture of proteinaceous material and an alkaline metal ligonsulfonate subjected to the acid hydrolysis and then oxidation, which when applied to plants and trees as a spray, or as an addition to the root zone soil, imparts freeze resistance to the plants and trees.

U.S. Pat. No. 2,013,063 discloses the use of spraying a plant with an aqueous wax emulsion, containing a colloidal earth, an ammonium salt of a drying acid, i.e., unsaturated fatty acids such as those derived from soya, fish or beans, whereby a permeable antidessicant film is formed.

U.S. Pat. No. 2,198,991 discloses a method for protecting living trees and plants from sunscald, borer and fungus injury by treating the trunks and branches with an aqueous emulsion comprising a paraffin wax, an ammonium salt of a drying acid, as defined in U.S. Pat. No. 2,013,063, a colloidal earth and finely divided aluminum.

There is also prior art that teaches the use of various oils, including fish oils, as a useful physical component to optimize stability of a plant protecting suspension of an active ingredient. For example, U.S. Pat. Nos. 4,826,863 and 4,734,432, disclose the use of various oils, including paraffin, soya, fish and mineral oils, together with, inter alia, the active ingredient such as a fungicide or herbicide, to provide a stabilized plant protecting agent suspension.

U.S. Pat. No. 4,761,423 discloses the use of a vegetable, animal or mineral oil together with, inter alia, a fungicide or insecticide to form an improved seed dressing.

U.S. Pat. Nos. 3,728,454, 3,725,557 and 3,728,453 disclose the use of pine or fish oil, together with, inter alia, the active ingredient, alloxan or alloxantin, or dialuric acid, respectively, to inhibit the growth of herbs bacteria, fungi and other microorganisms.

There is a serious limitation to the above teachings, in that non-natural products are used to provide plants protection against fungal diseases.

The literature has recently reported that some unsaturated fatty acids, which are natural products, applied externally to the lower leaves of potato plants protected the upper leaves against a challenge infection of the late blight fungus *Phytophthora infestans* (see Cohen et al., "Systemic Resistance of Potato Plants Against *Phytophthora infestans* Induced by Unsaturated Fatty Acids", *Physiol. and Molecular Plant Pathol.* 38:255–263, 1991). However, there is a serious drawback to the use of the said unsaturated fatty acids, even when used with low application rates, those that were significantly effective in providing protection were phytotoxic to the potato leaves.

For these and other reason, there is thus a widely recognized need for effective natural products that can lie sprayed on plants to protect them against fungal diseases, that induce no phytotoxicity.

SUMMARY OF THE INVENTION

It has now been found that a natural product, fish oils, effectively protects the crop against fungal disease, without being phytotoxic. This is a surprising result and the mechanism of effective protection without phytotoxicity is difficult to understand. The present invention thus successfully addresses the shortcomings of the present art by the use of a natural product that effectively protects plants against fungal disease, without being toxic to said plants.

Fish oils, as used herein, refers to oils obtained from various fish, including cod, haddock, capelin, squid, hake, shark, halibut, menhaden sardine, herring, pollack, cuttle, mackerel, sand eel, anchovy, salmon and gadoid.

Such oils contain predominantly $C_{14}$ to $C_{22}$ saturated and unsaturated fatty acids in the form of mono-, di- and triglycerides.

Of the saturated fatty acids palmitic (16:0) was most prevalent (about 15%), myristic acid (14:0) was next (about 5%), and stearic acid (18:0) was least prevalent (about 3%). Fish oils contained a variety of mono-, di- and polyunsaturated (PUFA) fatty acids with oleic acid (18:1 n9) most abundant (about 10–30%). Processed (purified) oils contained less oleic acid and increasing proportion of PUFA, especially linoleic (18:2), EPA (eicosapentaenoic 20:5 n3) and DHA (docosohexaenoic 22:6 n3). Other unsaturated fatty acids are: vaccenic acid (18:1 n7), linolenic acid (18:3 n3), eicosenoic acid (20:1 n9), octadecatetraenoic acid (18:4 n3), eicosadienoic acid (20:2 n6), eicosatrienoic acid (20:3 n3), arachidonic acid (20:4 n6), erucic or brassidic acid (22:1 n9), docospentaenoic acid (22:5 n3) and docostetraenoic acid (22:4 n6). Total omega 3 fatty acids reached about 70% in some of the oils. Two emulsified oils from Nippon (Iapan) contained 5% lecithin and 0.05% ethoxyquinoline. All oils contained antioxidants, vitamin A, vitamin D, and traces of free fatty acids. The antioxidants, viatamin A and vitamin D were each tested separately and were not found to provide protection against diseases.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
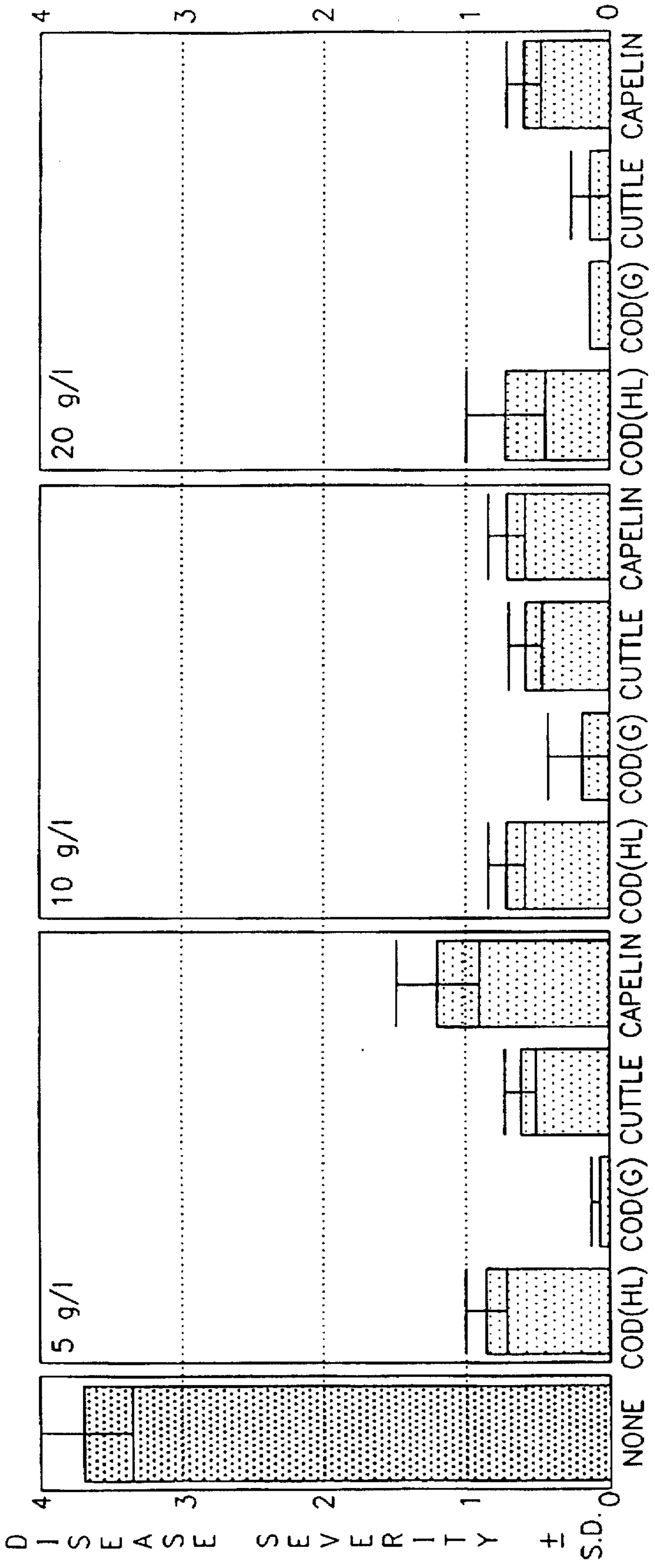
FIG. 1. Late blight development in potato (cv. Alpha) plants treated with four fish oils. Plants were sprayed with fish oil homogenate in water (0.5, 1, 2%) on their adaxial (upper) leaf surfaces and challenged with *Phytophthora infestans* (isolate MR-1, 5000 sporangia/ml) 2 days later. Disease records (0–4 scale) were taken 4 days after challenge. Bars represent standard deviation of the mean (n=3).

Preferred fish oils were those containing about 1% to about 40% by weight of one, or a combination of, fatty acids selected from the following: myristoleic, palmitic, palmitioleic, linolenic, linoleic, arachidonic, eicaspentenoic and docosohexaenoic, present as a monoglyceride, diglyceride or triglyceride, the free fatty acid being present in trace amounts. Particularly preferred fish oils are those containing about 5% to about 35% by weight of one, or a combination of, fatty acids selected from the following: palmitic, linoleic, arachidonic, eicaspentenoic and docosohexaenoic present as a monoglyceride, diglyceride or triglyceride.

The fish oils will typically be applied to the seed, tuber or foliage surfaces of the crop. When applied to the foliage, they will be used before the onset or after the initial signs of fungal attack. The amount of fish oil to be employed will be sufficient to induce the local and/or systemic resistance of the crop to control the fungal disease and will vary depending on such factors as the crop, species of fungi to be controlled, the type of treatment (for example, seed treatment, tuber treatment or foliage spraying or dusting), the condition of the crop and the particular fish oil used.

As a tuber or seed dressing, acceptable results may be obtained by employing from 0.1 to 1 kg of fish oil per 100 kg of tuber or seed.

As an application to the crop or its locus, the fish oil will be applied to the crops or to soil with a dosage rate in the range of from about 0.5 to about 10 kg/ha, with application being repeated as necessary, typically at intervals of every one to three weeks.

In practice, the fish oils will be applied in compositions containing the fish oil in association with an agriculturally acceptable diluent, such diluent typically being water and/or acetone. Such compositions for direct application to the crop will typically contain from about 0.05 to about 10% by weight fish oil, preferably from about 0.1 to about 5% by weight, with application being repeated as necessary, typically at intervals of every one to three weeks.

EXAMPLES

Plants.

Most experiments were conducted with the potato (*Solanum tuberosum L*) cultivar Alpha. Some experiments were dome with the cultivar Bintje. Plants were grown from whole tubers in sand:peat:vermiculite mixture (1:1:1 w/w) in the greenhouse (18°–24° C.) and were fertilized twice a week with 1% NPK (20:20:20). One tuber was sown in each pot (1:1). At ~4 weeks after sowing, plants having 3–5 stems/pot with ~10 compounds leaves/stem, were taken for experimentation.

Pathogen.

The metalaxyl-resistant isolate MR1 of *Phytophthora infestans* (Mont.) de Bary was mostly used. Some experiments were also conducted with other Israeli isolates and isolate S-49 from Switzerland (courtesy of U. Gisi, Sandoz Agro Research, Basel).

Fish oils.

Seven fish oils were obtained from the UK (Seven Seas, Hull, UK), nine from Japan (Nippon Chemical Feed Co. Ltd, Hokkaido, Japan), one from Norway (Jahres Sandefjord, Norway), two from B. Koven (National Institute for Oceanography, Eilat, Israel) and two were bought in local stores.

Spray and inoculation.

Aqueous homogenates of fish oils were obtained by homogenizing fish oil in water in a Kinematica (Basel, Switzerland) homogenizer operated at 27,000 rpm for 2 min. Acetone solutions were prepared by dissolving fish oil in analytical acetone. Oils were sprayed onto the adaxial (upper) leaf surfaces of potato or tomato plants (about 10 ml/plant) using a chromatography glass atomizer at an air pressure of 0.5 bar. Plants sprayed with water or acetone served as controls. Plants were placed in a growth chamber at 20° C. (12 h light per day, 120 μE $m^{-2}$ $s^{-1}$, CW fluorescent lamps supplemented with incandescent light) until challenge inoculated.

Freshly produced sporangia of *P. infestans* were harvested into ice-cold double-distilled water from potato tuber slices (cv. Alpha) inoculated a week earlier and kept at 13° C. Sporangia concentration was adjusted to 2500 or 5000 per ml and sprayed onto the abaxial or adaxial leaf surfaces of potato plants (about 15 ml per pot.). Inoculated plants were placed in a dew chamber in the dark at 18° C. for 20 h to ensure infection and then transferred to a growth chamber at 20° C. (as above) for symptom development.

Disease severity was visually estimated using a 0–4 scale as follows: 0=no disease; 0.05=one or 2 lesions per pot; 0.1=3–10 lesions; 0.5=11–50 lesions, about 10% of the foliage area occupied with lesions; 0.75=about 15–20% of the foliage is blighted; 1, 2 and 3=about 25, 50 and 75% of the leaf area blighted, respectively; and 4=plants are fully blighted. In some experiments lesion number and size were recorded.

I. Local Protection

Figure 2B:
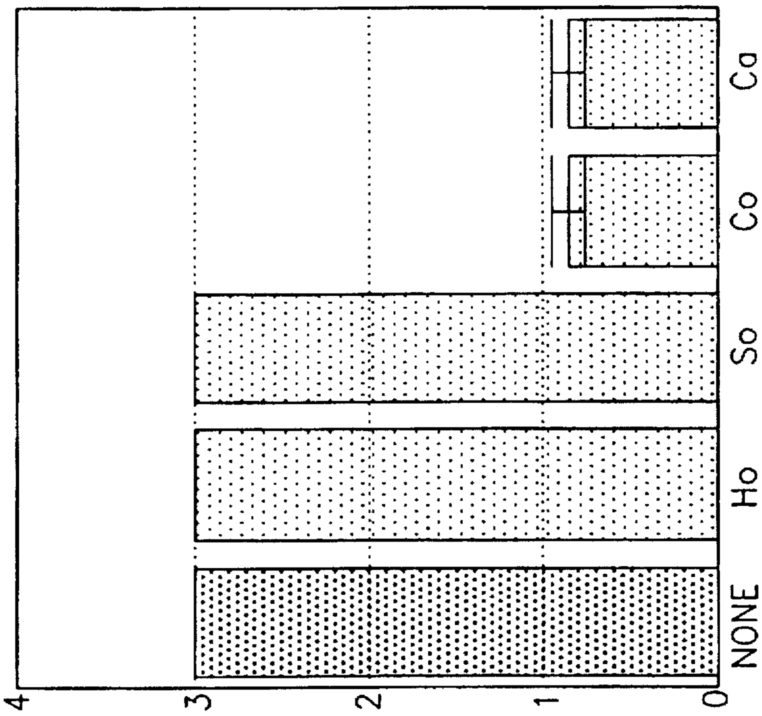
FIG. 2. A comparison between fish oils and vegetable oils in protecting potato (A) and tomato (B) plants against *Phytophthora infestans*. Plants were sprayed on upper leaf surface with hohoba oil, soybean oil, cod liver oil HL or capelin oil (1% in water) and challenged on the treated surfaces with the fungus (5000 sporangia/ml, isolate MR-1) 2 days after spray. Disease records (0–4 scale) were taken 5 days after challenge. Bars represent standard deviation of the mean (n=3).
Figure 2A:
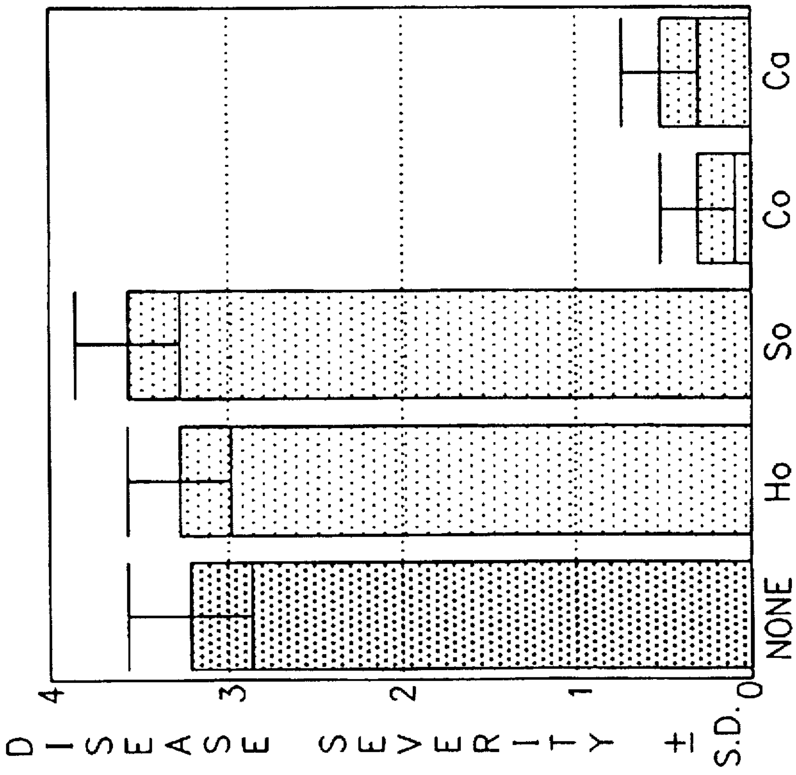

Fish oils were sprayed (as water homogenates) onto the adaxial (upper) leaf surfaces of potato plants (cv. Alpha) and challenged with *P. infestans* on the treated adaxial leaf surfaces 2 days later. Results presented in FIG. 1 show that plants treated with fish oils were protected (68–99%) against the blight infection. Protection increased slightly with increasing the oil concentration from 0.5 to 2%. Cod liver oil G was most effective providing >95% protection at all concentrations used. Vegetable oils (soybean and hohoba)

had no protective activity against late blight in either potato (FIG. 2A) or tomato (FIG. 2B). Fish oils provided 84–91% in potato and 75% protection in tomato (FIG. 2).

Figure 3:
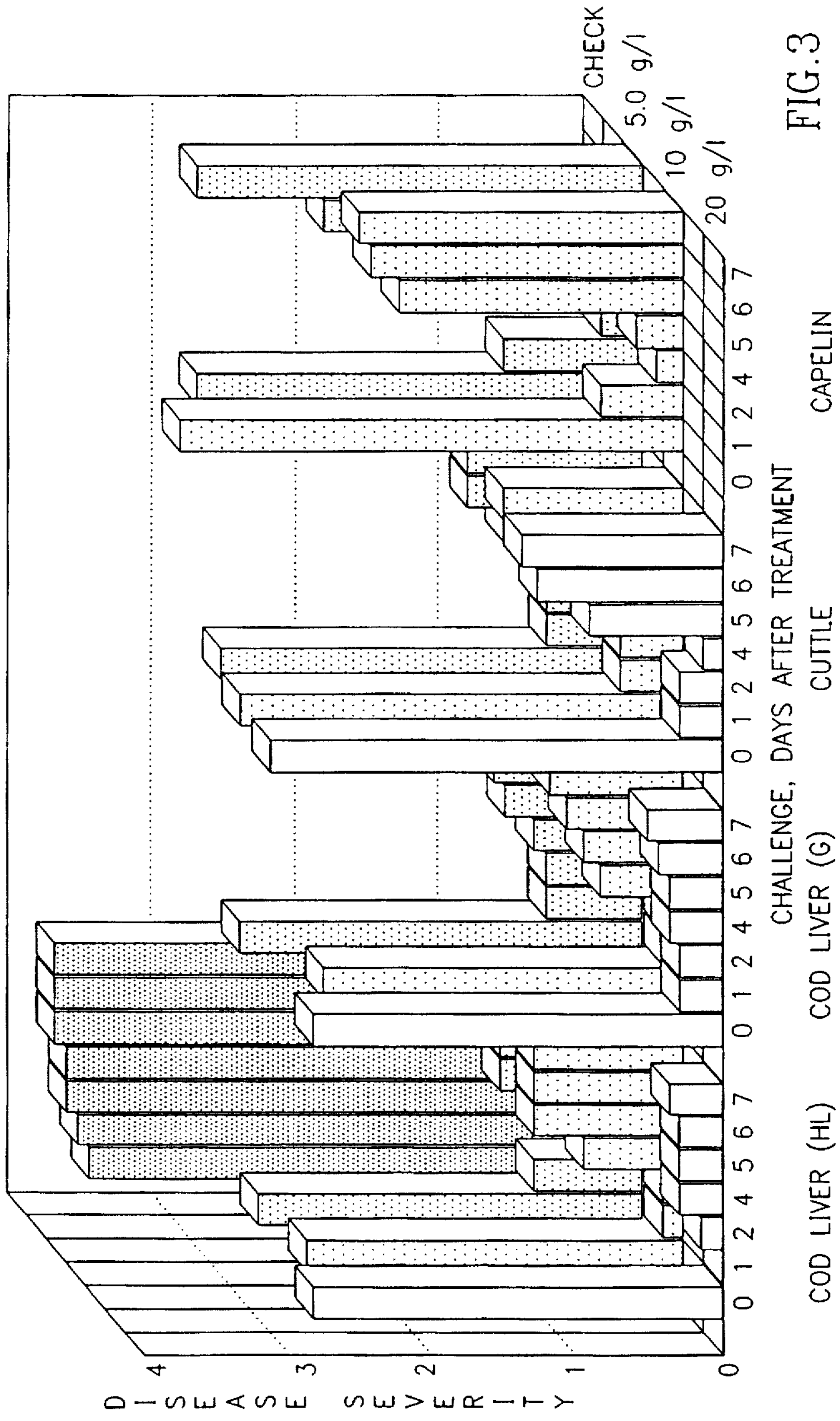
FIG. 3. Time-dependent efficacy of fish oils in controlling late blight in potato (cv. Alpha). Cod liver oil HL, cod liver oil G, cuttle oil and capelin oil were sprayed (0.5, 1 and 2% in water) on the upper leaf surfaces and plants were challenged on the treated surfaces with *Phytophthora infestans* (2500 sporangia/ml, isolate MR-1) at 0, 1, 2, 4, 5, 6 and 7 days after spray. Disease records were taken 4 days after challenge (n=3).

These four fish oils were similarly applied to potato plants but plants were challenge inoculated at various time-intervals after spray. Interestingly enough, oils had a minor protective activity, at either 0.5, 1 or 2%, in plants challenged immediately after the spray had dried off (day 0, about 2 h after spray). Substantial protection, however, was observed in plants challenged 1 day, or later, up to 7 days, after spray (FIG. 3). The residual protective activity depended on the fish oil used and on its concentration. Cod liver oil G was the best performing at 0.5 and 1% and cod liver oil HL at 2% whereas capelin oil was the least effective at 0.5% and 1% capelin oil was phytotoxic at 2%. Increasing the oil concentration increased protective efficacy of cod liver oils and cuttle oil (FIG. 3). Similar experiments conducted with 4% cod liver oil HL showed about 20% protection in potato plants challenged in day 0 and about 90% protection in plants challenged at 3–10 days after oil application.

Figure 4:
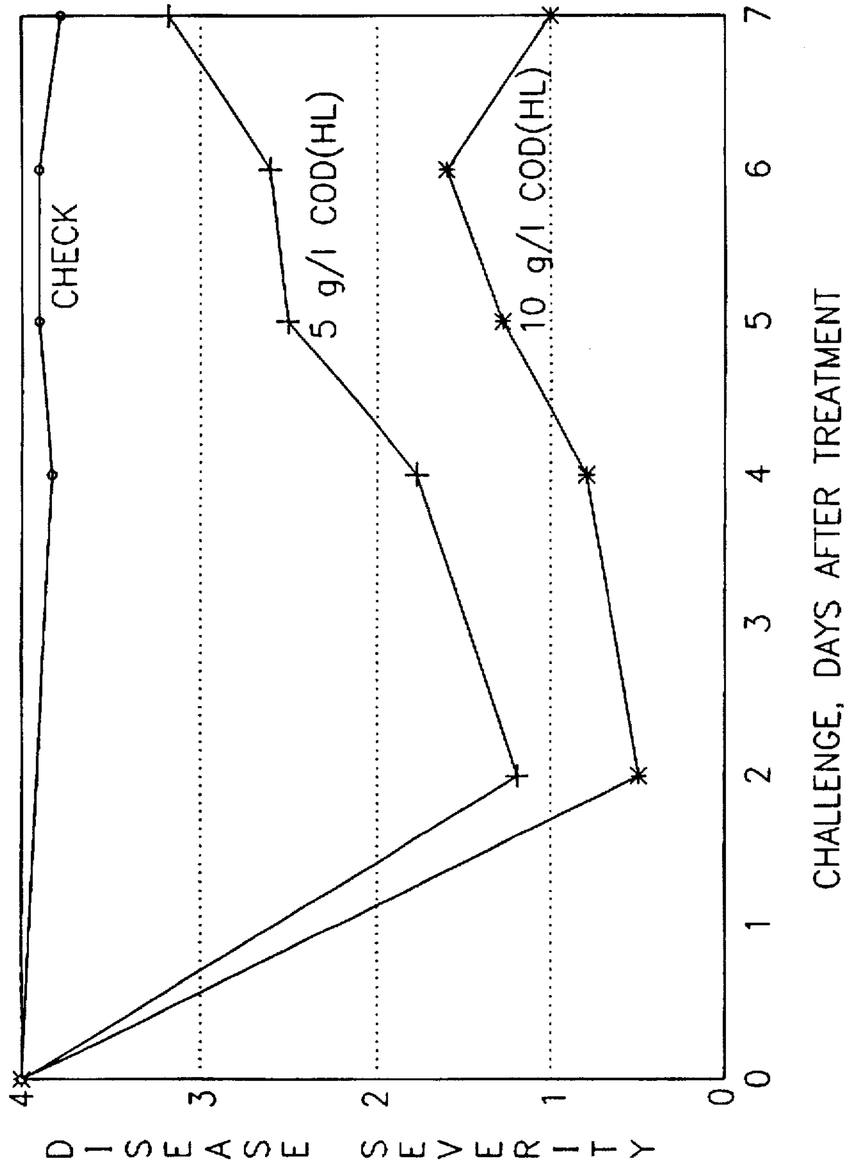
FIG. 4. Time-dependent efficacy of cod liver oil HL (0.5 and 1% in water) in controlling late blight caused by *Phytophthora infestans* in tomato plants (cv. Florida Basket). Plants were challenged (2500 sporangia/ml) at the various time intervals indicated after spray with fish oil. Fish oil and challenge were both applied to adaxial (upper leaf surfaces). Disease was recorded 4 days after challenge.

Cod liver oil HL in water also protected tomato plants (cv. Florida Basket) against late blight in the manner described for potato. Protection was dependent on the interval period between spray and challenged as well as on oil concentration (FIG. 4).

Acetone solutions of cod liver oil HL applied to upper leaf surfaces of potato plants 3 days before challenge, provided 67, 80, 88 and 96% protection at concentrations (w/v) of 0.25, 0.5, 1 and 2%, respectively. EPAX-GT 5500 applied similarly provided 93, 93 and 99% protection at 0.25, 0.5 and 1% respectively. It was slightly phytotoxic at 1%.

Sixteen other fish oils were tested for their possible protection against late blight. All were applied at 1% in water homogenates to the adaxial leaf surface of potato plants (cvs. Alpha or Bintje) and tomato plants (cvs. Baby and Florida Basket) and challenged with *P. infestans* (MR-1 or S-49) at 1, 2, or 3 days after spray.

Results (Table 1) varied between experiments and amongst oils. Generally, all oils were effective in protecting the plants against the blight. Mean protection values ranged between 67–91% for the various oils. Oils rich in EPA (EPA 28G from Nippon and EPAX GT 5500 from Jahres) provided the highest protection.

The above fish oils were dissolved so as to contain 0.1% equivalent of EPA in acetone and sprayed onto the adaxial leaf surfaces of potato plants (cv. Alpha). Control plants were sprayed with acetone alone. All plants were challenge-inoculated with *P. infestans* MR12 days after spray. Disease record were taken 4, 5 and 7 days postinoculation and % protection calculated relative to acetone-sprayed plants. All oils were highly effective in protecting against the blight (Table 2). The least effective were Nippon Nos. 4 and 6 indicating that EPA is not the only ingredient in fish oil responsible for protection.

II. Translaminar Protection

Figure 5B:
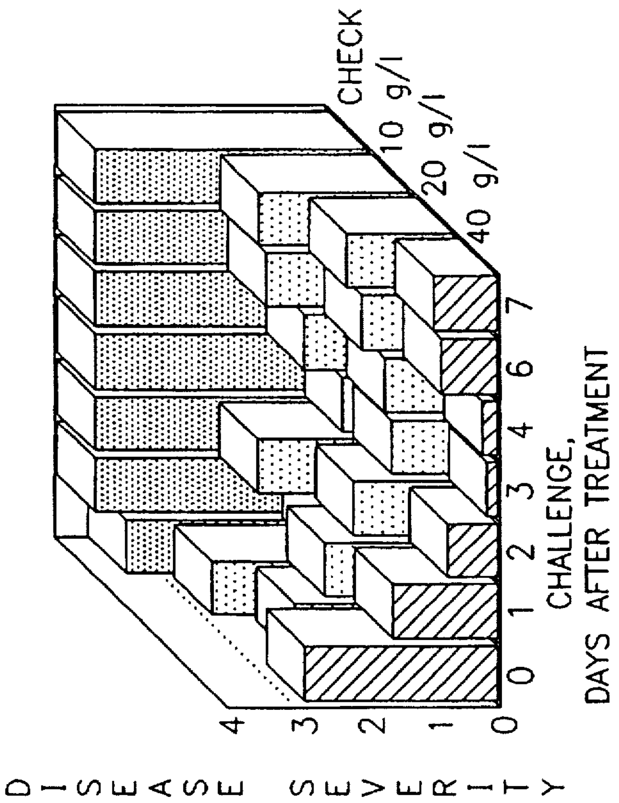
FIG. 5. Translaminar protection of untreated leaf surfaces of potato leaves against late blight with cod liver oil HL of various concentrations (1, 2 and 4% in water). Plants were sprayed on upper leaf surfaces with fish oil and then, at various time intervals after spray, challenged with *Phytophthora infestans* (2500 sporangia/ml, isolate MR-1) on either upper (A) or lower (B) surfaces. Disease records were taken 4 days after challenge.
Figure 5A:
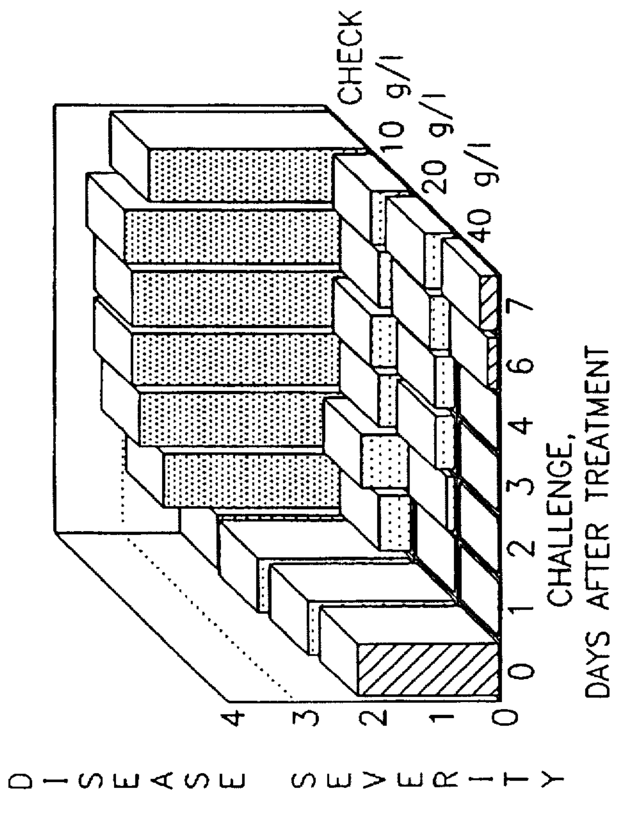

Potato plants were sprayed with fish oils on their adaxial (upper) surfaces and challenged with *P. infestans* on either their adaxial or adaxial (lower) surfaces. FIG. 5 presents data from an experiment in which challenge inoculation was applied to compound leaves detached from the nontreated plants and plants treated with various concentrations of cod liver oil HL in water. The oil-treated surfaces were highly protected (FIG. 5A) against the blight at all concentrations used (1–4%). Protection was prevalent at all sampling days except day 0 after spray (compare FIG. 3). The untreated leaf surfaces were protected, but to a lesser degree, with maximal protection observed in leaves inoculated at 3 days after spray (FIG. 5B). Protection of the untreated surfaces increased with increasing the oil concentration.

Another experiment was performed similarly with potato leaves detached and inoculated at various time intervals after spray. Leaves were challenge inoculated (2500 sporangia/ml)on their untreated surfaces. Percentage protection (relative m oil-nontreated leaves) in leaves inoculated at 0, 1, 2, 3, 4, 6, and 7 days after spraying with 1% cod liver oil HL in water was 37, 52, 45, 80, 65, 52 and 47%; with 2%–34, 37, 35, 85, 75, 67, and 57% and with 4%–39, 55, 77, 95, 90, 75 and 67%, respectively.

The following experiments were conducted with intact potato plants. Plants (cv. Alpha) were sprayed on upper leaf surfaces with either cod liver oil HL (1% w/v) in water or acetone, or with EPAX-GT 550 in water or acetone (1% w/v). Plants were challenged-inoculated on either the upper or the lower leaf surfaces at 1 or 5 days after spray. Results in Table 3 show that the upper, treated surfaces were strongly protected (82–99%) against the blight by both oils at 1 day after treatment. Inoculation made at 5 days reduced almost 2 fold the efficacy of cod liver oil HL but only slightly that of EPAX-GT 5500. When delivered in acetone both oils were slightly less effective (compared to both oils delivered in water) at 1 day but not at 5 days after treatment (Table 3). The lower untreated surfaces were protected to a degree if 69–85% at 1 day with acetone delivery, slightly less effective compared to water delivery. At 5 days after treatment cod liver oil HL lost its activity whereas EPAX-GT 5500 retained 48–59% of protective activity (Table 3). Similar results were obtained with potato plant cv. bintje (data not shown).

III. Systemic Protection

Figure 6B:
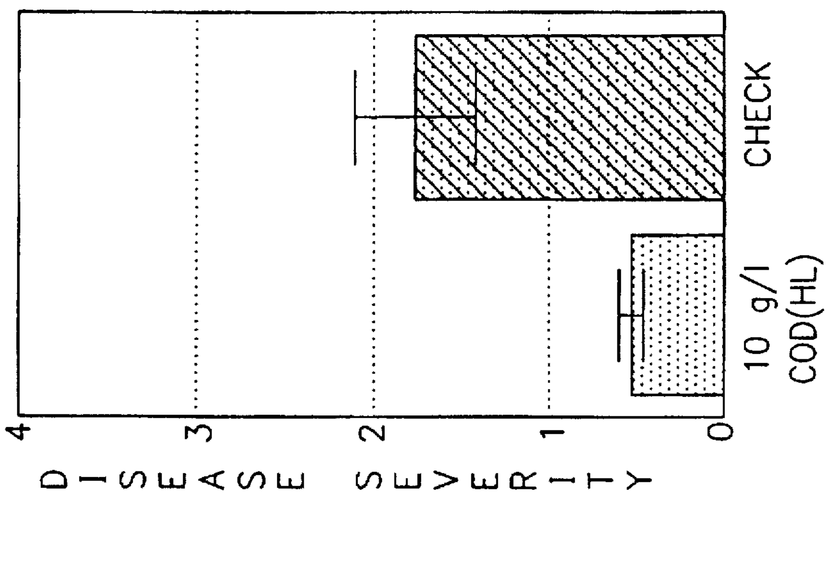
FIG. 6. Systemic protection of potato plants (cv. Alpha) by cod liver oil HL. Plants were sprayed on their 3 lower leaves with 2% fish oil and challenged with *Phytophthora infestans* (2500 sporangia/ml, isolate MR-1) 4 days later. Disease records were taken 3 days after challenge. A. Mean values per plant (the shaded area represents standard deviation of the mean (n=6)); B. Mean values per plant (bars represent standard deviation of the mean (n=6)).
Figure 6A:
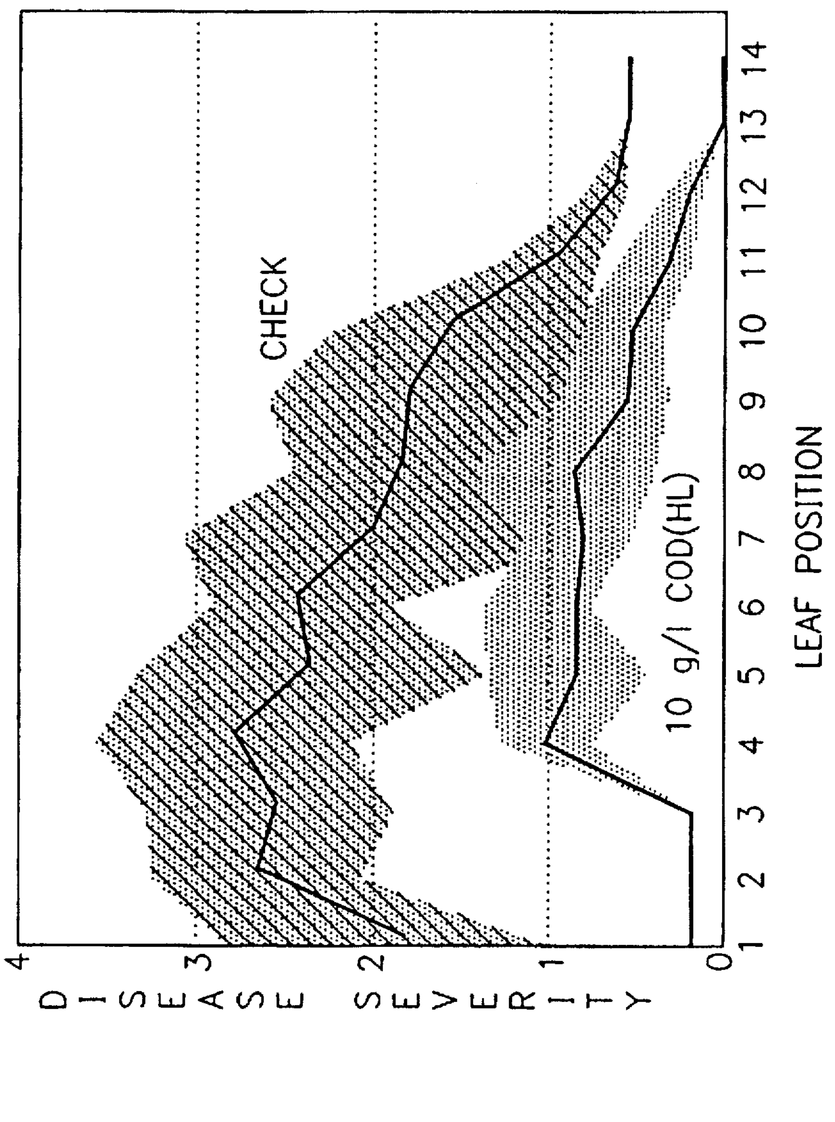

Eleven-leaf potato plants (cv. Alpha) were sprayed with cod liver oil HL 2% homogenate onto their 3 bottom leaves and challenge-inoculated 4 days later. Disease records taken 3 days post inoculation are presented in FIG. 6. Leaves on plants treated with oil were significantly less blighted compared to leaves of untreated-challenged plants (FIG. 6A). Mean percentage protection for all leaves was 74% (FIG. 6B). At four days post inoculation disease severity reached values of 3.7±0.21 and 1.4±0.48 for control and treated plants (62% protection), respectively.

In a second experiment 1 or 2% of cod liver oil HL homogenates were applied to the lower leaves of potato plants 5 days before challenge. Disease records taken 4 days after inoculation were 2.03±0.81 in untreated plants and 0.91±0.60 and 0.94±0.59 in plants treated with 1 and 2% oil (55 and 54% protection, respectively). Other experiments revealed that application of either cod liver oil HL (1%) or EPAX-GT 5500 (1%) to the 3 lower leaves of potato reduced the number of lesions on leaves 4–11. Control plants developed 55±15 lesions as against 23±6 and 15±1 in cod and EPAX-treated plants, respectively (58 and 73% protection).

TABLE 1

Local protective activity of fish oil homogenates (1%) in water against *Phytophthora infestans* in potato and tomato.

| Fish oil Source and No. | % protection Potato Alpha/1d MR-1 | Potato Alpha/3d MR-1 | Potato Bintje/2d S-49 | Tomato Florida Basket/1d MR-1 | Tomato Baby/2d MR-1 | Mean ± S.D. |
|---|---|---|---|---|---|---|
| Seven Seas, UK | | | | | | |
| 1 | — | 58 | 83 | 74 | 69 | 71 ± 10 |
| 2 | — | 71 | 70 | 78 | 78 | 74 ± 4 |
| 3 | — | 75 | 50 | 90 | 53 | 67 ± 19 |
| 4 | — | 67 | 61 | 82 | 76 | 72 ± 9 |
| 5 | — | 82 | 67 | 82 | 75 | 77 ± 7 |
| 6 | — | 78 | 85 | 89 | 75 | 82 ± 6 |
| 7 | — | 82 | 95 | 82 | 81 | 85 ± 7 |
| Nippon, Japan | | | | | | |
| 1 | 96 | 82 | — | 79 | — | 86 ± 9 |
| 2 | 89 | 79 | — | 83 | — | 84 ± 5 |
| 3 | 91 | 83 | — | 83 | — | 86 ± 5 |
| 4 | 85 | 56 | — | 86 | — | 76 ± 17 |
| 5 | 95 | 64 | — | 72 | — | 77 ± 16 |
| 6 | 78 | 69 | — | 68 | — | 72 ± 6 |
| 7 | 89 | 81 | — | 75 | — | 82 ± 7 |
| 8 | Phytotoxic | Phytotoxic | — | 92 | — | — |
| 9 | 80 | 94 | — | 96 | — | 90 ± 9 |
| Health Life, UK | | | | | | |
| Cod liver oil HL | 95 | — | — | — | — | — |
| Jahres, Norway | | | | | | |
| Epax GT 5500 | — | 89 | — | 93 | — | 91 ± 3 |

Number of days lapsed between fish oil application and challenge inoculation. Isolate MR-1 was inoculated at 5000 and 2500 sporangia/ml on potato and tomato, respectively. Isolates S-49 was applied at 7000 sporangia/ml. Disease records were taken at 5 days after inoculation when controi plants (untreated with fish oil) exhibited 80–90% of their foliage blighted.

TABLE 2

Local protection of potato plants (cv. Alpha) against *Phytophthora infestans* by fish oils dissolved in acetone

| Fish oil, Source and No. | Original EPA conc. % | Conc. used % w/v | % Protection 4d | % Protection 5d | % Protection 7d |
|---|---|---|---|---|---|
| Seven Seas, UK | | | | | |
| 1 | 7.5 | 1.3 | 92 | 90 | 83 |
| 2 | 5.8 | 1.7 | 99 | 99 | 96 |
| 3 | 5.4 | 1.85 | 91 | 85 | 81 |
| 4 | 9.6 | 1.0 | 90 | 84 | 85 |
| 5 | 8.6 | 1.2 | 93 | 92 | 83 |
| 6 | 13.8 | 0.72 | 96 | 95 | 87 |
| 7 | 14.6 | 0.69 | 95 | 91 | 85 |
| Nippon, Japan | | | | | |
| 1 | 13.1 | 0.76 | 85 | 84 | 79 |
| 2 | 14.6 | 0.68 | 97 | 92 | 66 |
| 3 | 11.0 | 0.91 | 90 | 91 | 73 |
| 4 | 10.0 | 1.0 | 78 | 81 | 58 |
| 5 | 14.2 | 0.71 | 93 | 90 | 85 |
| 6 | 15.3 | 0.65 | 71 | 72 | 37 |
| 7 | 13.6 | 0.73 | 98 | 96 | 91 |

TABLE 2-continued

Local protection of potato plants (cv. Alpha) against *Phytophthora infestans* by fish oils dissolved in acetone

| Fish oil, Source and No. | Original EPA conc. % | Conc. used % w/v | % Protection 4d | % Protection 5d | % Protection 7d |
|---|---|---|---|---|---|
| 8 | 28.4 | 0.35 | Phytotoxic | | |
| 9 | 23.5 | 0.43 | 97 | 88 | 79 |
| Jahres, Norway* | | | | | |
| Epax GT 5500 | 32.8 | 0.3 | 97 | 98 | 87 |

Plants were inoculated with 2500 sporangia/ml of isolate MR1. control plants, treated with acetone. showed 56 ± 17, 93 ± 4 and 100 ± 0% of their foliage blighted at 4,5 and 7 days after inoculation, respectively.

*Jahres Fabrikker, Norway

TABLE 3

Local and translaminar activity of fish oils against *Phytophthora infestans* in potato plants

| Treatment applied to upper surface | Upper surface inoculated days after treatment 1d* disease severity | % Protection | 5d disease severity | % Protection | Lower surface inoculated days after treatment 1d disease severity | % Protection | 5d disease severity | % protection |
|---|---|---|---|---|---|---|---|---|
| None | 4.0 ± 0 | — | 4.0 ± 0 | — | 4.0 ± 0 | — | 3.67 ± 0.47 | — |
| Acetone | 4.0 ± 0 | — | 4.0 ± 0 | — | 4.0 ± 0 | — | 3.82 ± 0.23 | — |
| Cod liver oil HL 1% in water | 0.08 ± 0.02 | 98 | 2.0 ± 0 | 50 | 1.0 ± 0.6 | 75 | 3.0 ± 0 | 18 |
| Cod liver oil HL 1% in acetone | 0.70 ± 0.1 | 82 | 1.67 ± 0.47 | 58 | 1.25 ± 0.5 | 69 | 3.33 ± 0.23 | 15 |
| Epax GT 5500 1% in water | 0.03 ± 0.02 | 99 | 0.67 ± 0.11 | 83 | 0.60 ± 0 | 85 | 1.5 ± 0 | 59 |
| Epax GT 5500 1% in acetone | 0.43 ± 0.17 | 89 | 0.58 ± 0.12 | 85 | 1.0 ± 0 | 75 | 2.0 ± 0 | 48 |

*Interval period, days, between oil application and challenge inoculation. Plants were challenged with 2500 sporangia/ml of isolate MR-1. Disease records were taken 7 days after inoculation.

Formulation Example I

Emulsion Concentrate 25 parts by weight of a fish oil, 65 parts of xylene, 10 parts of the mixed reaction product of an alklphenol with xyleneoxide and calcium-dodecyl-benzene sulphonate are thoroughly mixed until a homogeneous solution is obtained. The resulting emulsion concentrate is diluted with water before use.

Other formulations may include a delayed release composition, conventional carriers, diluents and/or adjuvants. Such compositions may be produced in conventional manner, e.g., by mixing the active ingredient with a carrier and other formulating ingredients with the aid of a Polytron.

Concentrate forms of compositions generally contain between about 2 and 80%, preferably between about 5 and 70% by weight of fish oil. Application forms of formulation may, for example, contain from 0.01% to 20% by weight, preferably from, 0.01% to 5% by weight of fish oil.

Depending on circumstances, the compounds of this invention may be used in association with metal salts of, for example, copper, zinc, manganese, or with pesticides, such as fungicides, insecticides, acaricides, herbicides or plant growth regulating agents in order to enhance their activity or to widen their spectrum of activity.

Formulation Example II

Seed or Tuber Dressing 25 parts by weight of a fish oil is absorbed on a carrier comprising 15 parts of fine silica and 44 parts of fine kaolin with the aid of small amount of a volatile solvent such as acetone. The resulting powder is first allowed to dry, and is then combined with 15 parts of dialkylphenoxypoly (ethylenoxy) ethanol, 0.5 parts of a colorant (e.g. crystal violet) and 0.5 parts of xanthan gum. This is mixed and ground in a contraplex mill at approximately 10,000 rpm to an average particle size of below 20 microns. The resulting formulation is applied to the seeds or tubers as an aqueous or organic suspension in an apparatus suitable for that purpose.

Fish oils according to this invention are effective at controlling a variety of phytopathogenic fungi belonging to Oomycetes, Ascomycetes, Basidiomycetes and Fungi Imperfecti families.

The following is a partial list of crops and corresponding diseases and organisms which can be controlled in accordance with the present invention.

| CROP | DISEASE | ORGANISM |
|---|---|---|
| potato | late blight | *Phytophthora infestans* |
| tomato | late blight | *Phytophthora infestans* |
| tobacco | blue bold | *Peronospora tabacina* |
| cucumber | downy mildew | *Pseudoperonospora cubessis* |
| grape | downy mildew | *Plasmopara viticola* |
| crucifers | downy mildew | *Peronospora parasitica* |
| cucumber | powdery mildew | *Sphaerotheca fuliginea* |
| cucumber | powdery mildew | *Erysiphe cichoracearum* |
| barley | powdery mildew | *Erysiphe graminis hordei* |
| wheat | powdery mildew | *Erysiphe graminis tritici* |
| rice | blast | *Pyricularia oryzae* |
| barley | leaf spot | *Cocchliobolus sativum* |
| bean | rust | *Uromyces appendiculatus* |
| wheat | rust | *Puccinia graminis tritici* |
| barley | rust | *Puccinia graminis hordei* |
| tomato | gray mold | *Botrytis cinerea* |
| cucumber | gray mold | *Botrytis cinerea* |
| grape | gray mold | *Botrytis cinerea* |
| grape | powder mildew | *Uncinulla necator* |

FURTHER EXAMPLES

Example 1

Protection of barley against *Erysiphe graminis* f. sp. *hordeit* by fish oils at 20° C.

Three-leaf plants were sprayed with acetone solutions of fish oil (1%, w/v) challenged 1 day later, and evaluated 10 days after challenge. The results are shown in the following table.

| Treatment | % infection relative to control |
|---|---|
| acetone (control) | 100 |
| Capelin oil 1% | 47 |
| Cod liver oil (G) 1% | 36 |
| Cod liver oil (UK) 1% | 26 |

Example 2

Protection of cucumbers against *Sphaerotheca fuliginea* by fish oils under field conditions (Israel) 3 sprays per season.

Fish oils were mixed with 0.05% emulgator (w/w) and water was added to obtain 0.5 or 1% fish oil in water (w/v). Plants were sprayed 3 times at weekly intervals. Evaluation was made 5 days after the last spray. The results are shown in the following table.

| Treatment | % leaf area infected | % disease control |
|---|---|---|
| None | 58 | 0 |
| Emulgator (0.05%) | 52 | 10 |
| Cod liver oil (UK) | | |
| 0.5% | 9 | 84 |
| 1% | 18 | 69 |
| Cod liver oil (G) | | |
| 0.5% | 13 | 78 |
| 1% | 6 | 90 |
| Cuttle oil | | |
| 0.5% | 6 | 90 |
| 1% | 10 | 83 |
| Capelin oil | | |
| 0.5% | 8 | 86 |
| 1% | 5 | 91 |

Example 3

Protection of cucumbers against *Psuedoperonospora cubensis* by fish oil at 20° C.

| Treatment | % leaf area infected | % disease control |
|---|---|---|
| None | 88 | 0 |
| Oxadixyl 250 mg/L | 88 | 0 |
| Cod liver oil 1% | 3 | 97 |
| Soybean oil 1% | 85 | 3 |

Example 4

Protection of cucumbers against *Psuedoperonospora cubensis* by fish oil under field conditions (Israel) 3 sprays.

Fish oils were mixed with 0.05% emulgator (w/w) and water was added to obtain 0.5 or 1% fish oil in water (w/v). Plants were sprayed 3 times at weekly intervals. Evaluation was made 5 days after the last spray. The results are shown in the following table.

| Treatment | % leaf area infected | % disease control |
|---|---|---|
| None | 35 | 0 |
| Emulgator (0.05%) | 43 | −23 |
| Cod liver oil (UK) | | |
| 0.5% | 2 | 94 |
| 1% | 6 | 83 |
| Cod liver oil (G) | | |
| 0.5% | 6 | 83 |
| 1% | 9 | 74 |
| Cuttle oil | | |
| 0.5% | 14 | 60 |
| 1% | 3 | 91 |
| Capelin oil | | |
| 0.5% | 8 | 77 |
| 1% | 15 | 57 |

-continued

Example 5

Protection of cucumbers against *Botrytis cinerea* by fish oil.

Plants at the first leaf stage were sprayed with homogenates of fish oil and challenged with *B. cinerea* 3 days later. Percentage of plants dead due to infection was counted 10 days after inoculation. The results are shown in the following table.

| Treatment | % dead plants |
|---|---|
| None | 100 |
| Cod liver oil 0.5% | 15 |
| Cod liver oil 1% | 0 |
| Cod liver oil 2% | 0 |

While the invention has been described with respect to a limited number of embodiments, it will be appreciated that many variations, modifications and other applications of the invention may be made.

What is claimed is:

1. A method for protecting cereal plant against powdery mildews caused by a fungus of the genus Erysiphe comprising the step of applying to the seed or foliage of the cereal plant or its locus a composition consisting essentially of a non-phytotoxic fish oil in an amount sufficient to non-phytotoxically inhibit infection of the cereal plant by a fungus of the genus Erysiphe.

2. The method of claim 1, wherein said fish oil is obtained from a fish selected from the group consisting of cod, haddock, capelin, squid, hake, shark, halibut, menhaden, sardine, herring, pollack, cuttle, mackerel, sand eel, anchovy, salmon and gadoid.

3. A method for protecting cucurbits against powdery mildews caused by at least one of the fungal species selected from the group consisting of *Sphaerotheca fuliginea* and *Erysiphe cichoracearum* comprising the step of applying to the seed or foliage of the cucurbit or its locus a composition consisting essentially of a non-phytotoxic fish oil in an amount sufficient to non-phytotoxically inhibit infection of the cucurbit by at least one of the fungal species selected from the group consisting of *Sphaerotheca fuliginea* and *Erysiphe cichoracearum*.

4. The method of claim 3, wherein said fish oil is obtained from a fish selected from the group consisting of cod, haddock, capelin, squid, hake, shark, halibut, menhaden, sardine, herring, pollack, cuttle, mackerel, sand eel, anchovy, salmon and gadoid.

5. A method for protecting grape plant against powdery mildews caused by a fungus of the genus Uncinulla comprising the step of applying to the seed or foliage of the grape plant or its locus a composition consisting essentially of a non-phytotoxic fish oil in an amount sufficient to non-phytotoxically inhibit infection of the grape plant by a fungus of the genus Uncinulla.

6. The method of claim 5, wherein said fish oil is obtained from a fish selected from the group consisting of cod, haddock, capelin, squid, hake, shark, halibut, menhaden, sardine, herring, pollack, cuttle, mackerel, sand eel, anchovy, salmon and gadoid.

7. A method for protecting cucurbits against downy mildews caused by a fungus of the genus Pseudonoperonospora comprising the step of applying to the seed or foliage of the cucurbit or its locus a composition consisting essentially of a non-phytotoxic fish oil in an amount sufficient to non-phytotoxically inhibit infection of the cucurbit by a fungus of the genus Pseudonoperonospora.

8. The method of claim 7, wherein said fish oil is obtained from a fish selected from the group consisting of cod, haddock, capelin, squid, hake, shark, halibut, menhaden, sardine, herring, pollack, cuttle, mackerel, sand eel, anchovy, salmon and gadoid.

9. A method for protecting crucifer plant against downy mildews caused by a fungus of the genus Peronospora comprising the step of applying to the seed or foliage of the crucifer plant or its locus a composition consisting essentially of a non-phytotoxic fish oil in an amount sufficient to non-phytotoxically inhibit infection of the crucifer plant by a fungus of the genus Peronospora.

10. The method of claim 9, wherein said fish oil is obtained from a fish selected from the group consisting of cod, haddock, capelin, squid, hake, shark, halibut, menhaden, sardine, herring, pollack, cuttle, mackerel, sand eel, anchovy, salmon and gadoid.

11. A method for protecting grape plant against downy mildews caused by a fungus of the genus Plasmopara comprising the step of applying to the seed or foliage of the grape plant or its locus a composition consisting essentially of a non-phytotoxic fish oil in an amount sufficient to non-phytotoxically inhibit infection of the grape plant by a fungus of the genus Plasmopara.

12. The method of claim 11, wherein said fish oil is obtained from a fish selected from the group consisting of cod, haddock, capelin, squid, hake, shark, halibut, menhaden, sardine, herring, pollack, cuttle, mackerel, sand eel, anchovy, salmon and gadoid.

13. A method for protecting cucumber plant against gray mold caused by the fungal species *Botrytis cinerea* comprising the step of applying to the seed or foliage of the cucumber plant or its locus a composition consisting essentially of a non-phytotoxic fish oil in an amount sufficient to non-phytotoxically inhibit infection of the cucumber plant by the fungus *Botrytis cinerea*.

14. The method of claim 13, wherein said fish oil is obtained from a fish selected from the group consisting of cod, haddock, capelin, squid, hake, shark, halibut, menhaden, sardine, herring, pollack, cuttle, mackerel, sand eel, anchovy, salmon and gadoid.

15. The method of claim 1, wherein said composition further comprises an agriculturally acceptable diluent.

16. The method of claim 3, wherein said composition further comprises an agriculturally acceptable diluent.

17. The method of claim 5, wherein said composition further comprises an agriculturally acceptable diluent.

18. The method of claim 7, wherein said composition further comprises an agriculturally acceptable diluent.

19. The method of claim 9, wherein said composition further comprises an agriculturally acceptable diluent.

20. The method of claim 11, wherein said composition further comprises an agriculturally acceptable diluent.

21. The method of claim 13, wherein said composition further comprises an agriculturally acceptable diluent.

* * * * *